United States Patent
Tan et al.

(10) Patent No.: US 10,495,603 B1
(45) Date of Patent: Dec. 3, 2019

(54) HIGH PERFORMANCE ISFET WITH FERROELECTRIC MATERIAL

(71) Applicant: GLOBALFOUNDRIES Singapore Pte. Ltd., Singapore (SG)

(72) Inventors: Shyue Seng Tan, Singapore (SG); Kiok Boone Elgin Quek, Singapore (SG); Eng Huat Toh, Singapore (SG); Lanxiang Wang, Singapore (SG)

(73) Assignee: GLOBALFOUNDRIES SINGAPORE PTE. LTD., Singapore (SG)

( * ) Notice: Subject to any disclaimer, the term of this patent is extended or adjusted under 35 U.S.C. 154(b) by 0 days.

(21) Appl. No.: 15/977,409

(22) Filed: May 11, 2018

(51) Int. Cl.
*G01N 27/403* (2006.01)
*G01N 27/414* (2006.01)
*H01L 29/786* (2006.01)
*H01L 29/78* (2006.01)
*H01L 29/06* (2006.01)
*H01L 21/28* (2006.01)

(52) U.S. Cl.
CPC ..... *G01N 27/4146* (2013.01); *H01L 29/0669* (2013.01); *H01L 29/40111* (2019.08); *H01L 29/78391* (2014.09); *H01L 29/78648* (2013.01)

(58) Field of Classification Search
CPC .......... G01N 27/4146; H01L 29/78391; H01L 29/0669; H01L 29/78648; H01L 21/28291
USPC ....................................................... 257/253
See application file for complete search history.

(56) References Cited

U.S. PATENT DOCUMENTS

| 5,757,054 A * | 5/1998 | Miyawaki ......... G02F 1/136277 257/347 |
| 8,940,569 B2 | 1/2015 | Bedell et al. |
| 2007/0210349 A1* | 9/2007 | Lu ............................. B82Y 5/00 257/252 |
| 2011/0147723 A1* | 6/2011 | Hodges, Jr. ......... H01L 51/0529 257/40 |
| 2016/0207761 A1* | 7/2016 | Alam ..................... H01L 29/515 |
| 2017/0333644 A1* | 11/2017 | Reboud ................ A61M 11/005 |
| 2018/0364169 A1* | 12/2018 | Anderson ........... G01N 21/6428 |

OTHER PUBLICATIONS

Kurzweil, "Metal Oxides and Ion-Exchanging Surfaces as pH Sensors in Liquids: State-of-the-Art and Outlook", Sensors, Jun. 23, 2009, 31 pages.
Huang et al., "A 64×64 1200fps CMOS Ion-Image Sensor with Suppressed Fixed-Pattern-Noise for Accurate High-throughput DNA Sequencing", IEEE, Symposium on VLSI Circuits Digest of Technical Papers, 2014, 2 pages.
Huang et al., "High Performance Dual-Gate Isfet with Non-ideal Effect Reduction Schemes in a SOI-CMOS Bioelectrical SoC", IEEE, 2015, 4 pages.

(Continued)

*Primary Examiner* — Tu-Tu V Ho
(74) *Attorney, Agent, or Firm* — David Cain; Andrew M. Calderon; Roberts Mlotkowski Safran Cole & Calderon, P.C.

(57) ABSTRACT

The present disclosure relates to semiconductor structures and, more particularly, to high performance ion sensitive field effect transistor (ISFET) with ferroelectric material and methods of manufacture. The structure includes: a substrate comprising a doped region; a gate dielectric material over the doped region; a ferroelectric material over the gate dielectric material; and a sensing membrane over the ferroelectric material.

18 Claims, 4 Drawing Sheets

(56) References Cited

OTHER PUBLICATIONS

Mu et al., "Silicon Nanowire Field-Effect Transistors—A Versatile Class of Potentiometric Nanobiosensors", IEEE, vol. 3, Apr. 22, 2015 16 pages.
Salahuddin et al., "Can the subthreshold swing in a classical FET be lowered below 60 mV/decade?", School of Electrical and Computer Engineering and NSF Network for Computational Nanotechnology (NCN), Jan. 2009, 4 pages.
Hu et al., "0.2V Adiabatic NC-FinFET with 0.6mA/J.lm ION and 0.1nA/J.lm IOFF", IEEE, 2015, 2 pages.
Hoffmann et al., "Direct Observation of Negative Capacitance in Polycrystalline FerroelectricHfO2", Materials Views, Advanced Functional Materials, 2016, 7 pages.
Perello et al., "High-performance n-type black phosphorus transistors with type control via thickness and contact-metal engineering", Nature Communications, Jul. 30, 2015, 10 pages.

* cited by examiner

HIGH PERFORMANCE ISFET WITH FERROELECTRIC MATERIAL

FIELD OF THE INVENTION

The present disclosure relates to semiconductor structures and, more particularly, to a high performance ion sensitive field effect transistor (ISFET) with ferroelectric material and methods of manufacture.

BACKGROUND

An ion-sensitive field-effect transistor (ISFET) is a field-effect transistor used for measuring ion concentrations in solution. ISFET is a key device used in DNA sequencing. The ISFET device can detect pH changes in the solution through DNA polymerase synthesis. For example, the changes monitored by a sensing membrane (e.g., $SiO_2$, $Si_3N_4$, $Al_2O_3$, $Ta_2O_5$, etc.) of the ISFET can be converted to electrical signals for measurements. More specifically, when the ion concentration (such as $H^+$) changes, the current through the transistor will change accordingly. A voltage between substrate and oxide surfaces arises due to an ion sheath.

SUMMARY

In an aspect of the disclosure, a structure comprises: a substrate comprising a doped region; a gate dielectric material over the doped region; a ferroelectric material over the gate dielectric material; and a sensing membrane over the ferroelectric material.

In an aspect of the disclosure, a negative capacitance ion sensitive device comprising a gate dielectric material, a ferroelectric material and a sensing membrane electrically connected in series.

In an aspect of the disclosure, a method comprises: depositing a gate dielectric material on a doped portion of a substrate; depositing a ferroelectric material on the gate dielectric material; depositing a dummy gate material on the ferroelectric material; depositing an interlevel dielectric material over the dummy gate material; forming contacts to source and drain regions of the substrate; opening the interlevel dielectric material to expose the dummy gate material; removing the dummy gate material to expose the ferroelectric material; and depositing a sensing membrane over the ferroelectric material and sidewalls of the opening.

BRIEF DESCRIPTION OF THE DRAWINGS

The present disclosure is described in the detailed description which follows, in reference to the noted plurality of drawings by way of non-limiting examples of exemplary embodiments of the present disclosure.

DETAILED DESCRIPTION

Figure 1:
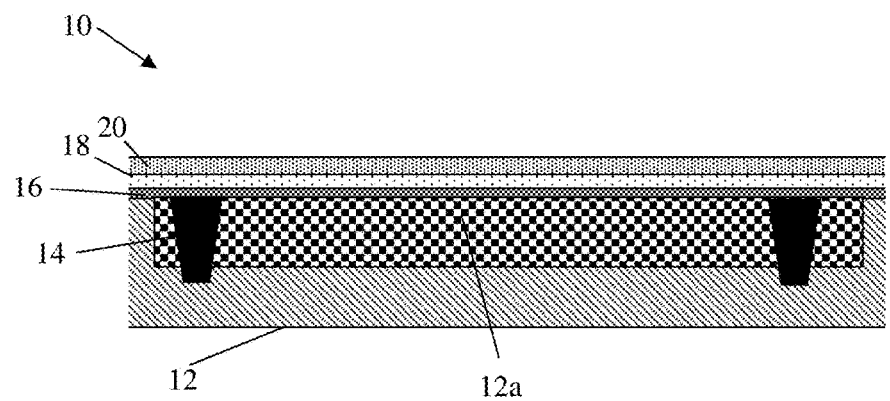
FIG. 1 shows a structure with ferroelectric material, amongst other features, and respective fabrication processes in accordance with aspects of the present disclosure.

The present disclosure relates to semiconductor structures and, more particularly, to a high performance ion sensitive field effect transistor (ISFET) with ferroelectric material and methods of manufacture. More specifically, the present disclosure describes a negative-capacitance ion-sensitive FET (NC-ISFET) with high sensitive to pH change by utilizing a stack of sensing layer/ferroelectric material/dielectric configuration to achieve voltage amplification and flexibility without hysteresis, and voltage division capability. Advantageously, the present disclosure provides a high sensitivity ISFET device with fast and accurate response.

In embodiments, the ISFET device includes a stack of sensing membrane, a ferroelectric layer and gate dielectric layer connected in series to form a negative capacitance ISFET device. In embodiments, the ferroelectric layer achieves a high pH sensitivity, compared to a conventional ISFET device. In further embodiments, the ISFET scheme can include a floating-gate type ISFET or other ISFET structures. The transistor channel material can include two-dimensional semiconductor (2D semiconductor), particularly transition metal dichalcogenides (TMDCs) and black phosphorus. For example, $MoS_2$, $MoSe_2$, $MoTe_2$, $WS_2$ and $WSe_2$ can be 2D semiconductor material implemented with the ISFET device.

The method of fabricating the ISFET device, as described in greater detail below, includes, e.g., forming a gate dielectric layer, followed by deposition of a ferroelectric layer and a dummy gate material on an active area. After patterning of the material, source and drain regions are formed in the underlying substrate, followed by contact formation, e.g., deposition of an interlevel dielectric material, contact etch and metal deposition in the interlevel dielectric material. A deposition of a passivation layer is provided over the interlevel dielectric material. A cavity (trench) is then opened in the interlevel dielectric material to expose and remove the dummy gate material, which then exposes the ferroelectric material. A sensing membrane is formed on the ferroelectric material. In this way, it is possible to form a high-sensitive NC-ISFET by $0<C_{cmos}/|C_{fe}|$ and $C_{sense}/C_{cmos}>1$, respectively.

The ISFET device of the present disclosure can be manufactured in a number of ways using a number of different tools. In general, though, the methodologies and tools are used to form structures with dimensions in the micrometer and nanometer scale. The methodologies, i.e., technologies, employed to manufacture the ISFET device of the present disclosure have been adopted from integrated circuit (IC) technology. For example, the structures are built on wafers and are realized in films of material patterned by photolithographic processes on the top of a wafer. In particular, the fabrication of the ISFET device uses three basic building blocks: (i) deposition of thin films of material on a substrate, (ii) applying a patterned mask on top of the films by photolithographic imaging, and (iii) etching the films selectively to the mask.

FIG. 1 shows a structure with ferroelectric material, amongst other features, and respective fabrication processes in accordance with aspects of the present disclosure. In particular, the structure 10 includes a substrate 12 with shallow trench isolation regions 14. In embodiments, the substrate 12 is any suitable semiconductor material. For example, the substrate 12 can be composed of any suitable material including, but not limited to, Si, SiGe, SiGeC, SiC, GaAs, InAs, InP, and other III/V or II/VI compound semiconductors. In embodiments, the substrate 12 includes a P-well 12a formed using conventional implantation methods such that no further explanation is required for an understanding of the present disclosure. In alternate embodiments, the well can also be an N-well.

In embodiments, the shallow trench isolation regions 14 can be formed by conventional lithography, etching and deposition methods. For example, a resist formed over the substrate 12 is exposed to energy (light) to form a pattern (opening). An etching process with a selective chemistry, e.g., reactive ion etching (RIE), will be used to form one or more trenches in the substrate 12 through the openings of the resist. The resist can then be removed by a conventional oxygen ashing process or other known stripants. Following the resist removal, insulator material (e.g., oxide) can be deposited by any conventional deposition processes, e.g., chemical vapor deposition (CVD) processes. Any residual insulator material on the surface of the substrate 12 can be removed by conventional chemical mechanical polishing (CMP) processes.

Still referring to FIG. 1, a gate dielectric material 16 is deposited on the substrate 12. In embodiments, the gate dielectric material 16 can be deposited by conventional deposition processes, e.g., atomic layer deposition (ALD) or plasma enhanced vapor deposition (PEVD) methods. The gate dielectric material 16 can be an oxide material ($SiO_2$) or a high-k dielectric material. For example, the gate dielectric material 16 can be e.g., $HfO_2Al_2O_3$, $Ta_2O_3$, $TiO_2$, $La_2O_3$, $SrTiO_3$, $LaAlO_3$, $ZrO_2$, $Y_2O_3$, $Gd_2O_3$, and combinations including multilayers thereof. The gate dielectric material 16 can be deposited to a thickness of about 10 nm or less, as one example, depending on the technology node.

A ferroelectric material 18 is deposited on the gate dielectric material 16. In embodiments, the ferroelectric material 18 can be any ferroelectric material. For example, the ferroelectric material 18 can be lead zirconate titanate (PZT), $PbZr/TiO_3$, $BaTiO_3$, $PbTiO_3$, lead lanthanum zirconate titanate (PLZT), $SrBi_2Ta_2O_9$, etc. In embodiments, high-k materials also can be ferroelectric including, e.g., $HfO_2$, HfAlOx, and HfZrOx. The ferroelectric material 18 can be deposited to a thickness of about 10 nm or less, as one example, depending on the technology node. In embodiments, the ferroelectric material 18 is deposited by ALD or PEVD, as examples. A dummy gate material 20 is deposited on the ferroelectric material 18. The dummy gate material can be, e.g., poly material.

Figure 2:
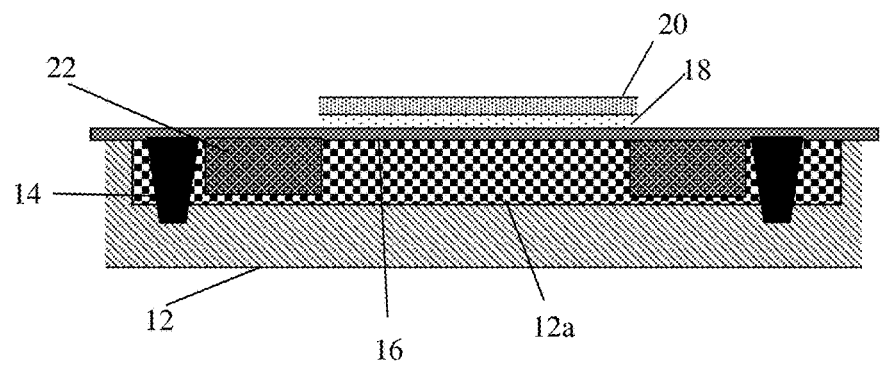
FIG. 2 shows a patterned ferroelectric material, amongst other features, and respective fabrication processes in accordance with aspects of the present disclosure.

Referring to FIG. 2, the gate dielectric material 16, ferroelectric material 18 and dummy gate material 20 are patterned by conventional lithography and etching processes. Source and drain regions 22 are then implanted into the substrate 12 by conventional ion implantation processes. The source and drain regions 22 are provided between the shallow trench isolation regions 14 and the patterned materials 16, 18, 20. The source and drain regions 22 can then undergo a silicide process.

As should be understood by those of skill in the art, the silicide process begins with deposition of a thin transition metal layer, e.g., nickel, cobalt or titanium, over the doped or ion implanted source and drain regions 22. After deposition of the material, the structure is heated allowing the transition metal to react with exposed silicon (or other semiconductor material as described herein) in the active regions of the semiconductor device (e.g., source, drain, gate contact region) forming a low-resistance transition metal silicide. Following the reaction, any remaining transition metal is removed by chemical etching, leaving silicide contacts in the active regions of the device. It should be understood by those of skill in the art that silicide contacts will not be required on the devices, when a gate structure is composed of a metal material.

Figure 3:
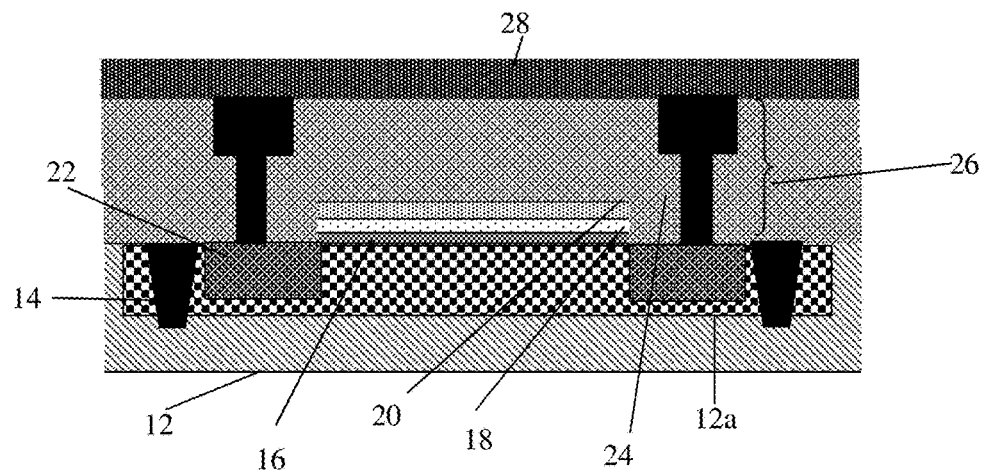
FIG. 3 shows contacts to source and drain regions, amongst other features, and respective fabrication processes in accordance with aspects of the present disclosure.

In FIG. 3, an interlevel dielectric material 24 (e.g., oxide) is deposited over the patterned materials 16, 18, 20 using conventional deposition processes, e.g., chemical vapor deposition (CVD) process. Source and drain contacts and wiring layers 16 are formed in the interlevel dielectric material 24. In embodiments, the source and drain contacts and wiring layers 16 can be formed by single or dual damascene processes using conventional lithography, etching and deposition processes. In embodiments, the source and drain contacts and wiring layers 16 will be in direct contact with the source and drain regions 22 (e.g., silicide contacts), and extend to upper wiring layers or bond pads, etc.

A passivation layer 28 is formed over the source and drain contacts and wiring layers 16 and interlevel dielectric material 24. The passivation layer 28 can be SiN, for example, deposited by a conventional CVD process. In alternative embodiments, the passivation layer can be nitride, $SiO_2$ or oxide as further examples.

Figure 4:
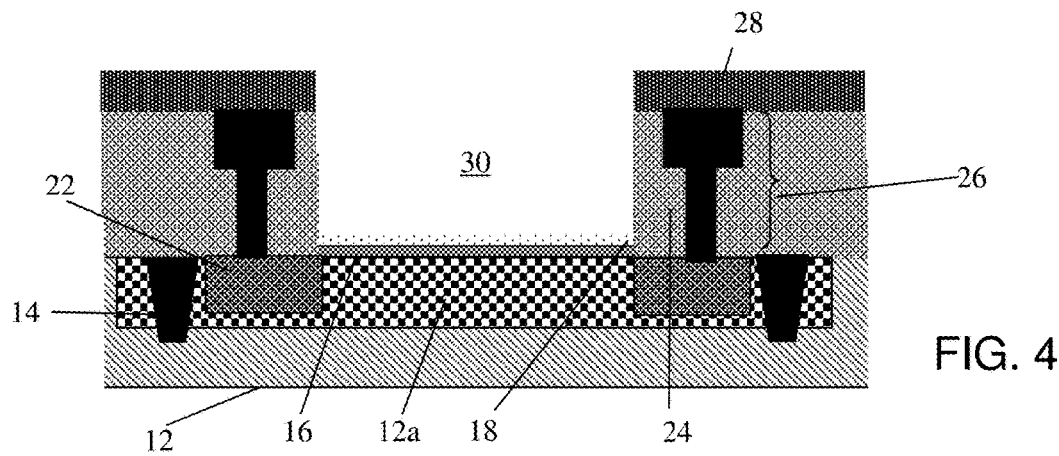
FIG. 4 shows removal of a dummy gate material to expose the patterned ferroelectric material, amongst other features, and respective fabrication processes in accordance with aspects of the present disclosure.

As shown in FIG. 4, a trench or cavity 30 is formed in the passivation layer 28 and the interlevel dielectric material 24, exposing the dummy gate material 20. The dummy gate material 20 is then removed by a conventional etching process, e.g., RIE, with a selective chemistry to the material of the dummy gate material 20. The removal of the dummy gate material 20 will expose the ferroelectric material 18.

Figure 5:
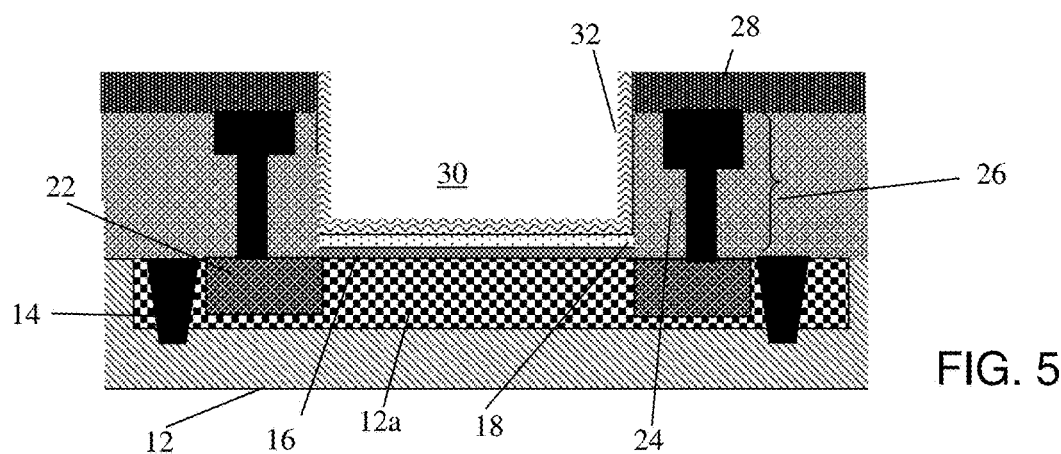
FIG. 5 shows a sensing membrane on the patterned ferroelectric material, amongst other features, and respective fabrication processes in accordance with aspects of the present disclosure.

In FIG. 5, a sensing membrane 32 is deposited in the trench 30, covering the ferroelectric material 18. In embodiments, the sensing membrane 32 can be $Al_2O_3$ deposited by an ALD process, as an example. The sensing membrane 32 can also be other materials such as, e.g., $SiO_2$, $Si_3N_4$, $Al_2O_3$, $Ta_2O_5$, $HfO_3$ or $TiO_2$, etc. Following the deposition of the sensing membrane 32, any excess material on the passivation layer 28 will be removed by a CMP process. In this way, the sensing membrane 32 is only in the trench 30 (e.g., over the ferroelectric material 18 and sidewalls of the trench 30). By using the combination of the sensing membrane 32 and the ferroelectric material 18, it is now possible to achieve >2x higher sensitive of pH change compared to a conventional structure.

Figure 6:
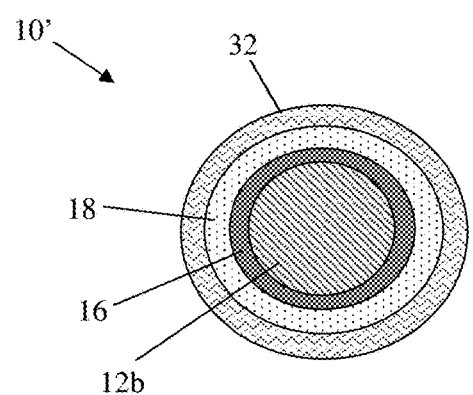
FIG. 6 shows a nanowire structure with ferroelectric material, amongst other features, and respective fabrication processes in accordance with aspects of the present disclosure.

FIG. 6 shows a nanowire structure with ferroelectric material, amongst other features, and respective fabrication processes in accordance with aspects of the present disclosure. In particular, the nanowire 10' includes a core material 12b of doped semiconductor material. In embodiments, the dopant can be a p-type dopant (e.g., phosphorous or arsenic) or an n-type dopant (e.g., boron or other group III species). A gate dielectric material 16 is deposited about the core material 12b. A ferroelectric material 18 is deposited about the gate dielectric material 16, with the sensing membrane 32 deposited about the ferroelectric material 18. The materials 12b, 16, 18 and 32 can be the same materials as described above, deposited in conventional deposition processes to form the nanowire 10'. In embodiments, the nanowire 10' can boost sensitivity by a change of conductance, e.g., 85 nS/pH.

Figure 7:
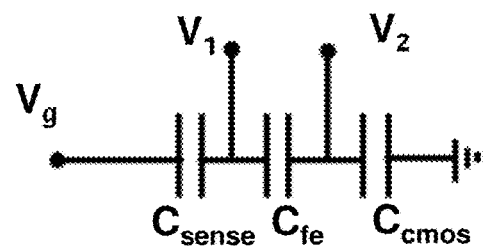
FIG. 7 shows a representative circuit of the structures shown in FIGS. 5 and 6.

FIG. 7 shows a representative circuit of the structures shown in FIGS. 5 and 6. In particular, the circuit includes capacitors $C_{sense}$, |Cfe| and $C_{cmos}$, in series. It should be understood by those of skill in the art that capacitor $C_{sense}$ is representative of the capacitance of the sensing membrane 32, |Cfe| is representative of the capacitance of the ferroelectric material 18 and $C_{cmos}$ is representative of the capacitance of the gate dielectric material 16 and/or substrate 12. Vg is voltage to ground; whereas, $V_1$ and $V_2$ are voltages to the source and drain regions.

The following shows proof of concept that the use of the ferroelectric material 18 will increase sensitivity of the ISFET and nanowire described herein.

Using a capacitor divider:

$$C_{sense}(Vg-V_1)=|Cfe|(V_1-V_2)=C_{cmos}(V_2) \quad \text{(Eq. 1)}$$

$$\text{For } |Cfe|(V_1-V_2)=C_{cmos}(V_2) \quad \text{(Eq. 2)}$$

$$|Cfe|V_1=C_{cmos}V_2+|C_{fe}|V_2$$

$$V_1/V_2=(|C_{fe}|+C_{cmos})/|C_{fe}|$$

$$V_2/V_1=|C_{fe}|/(|C_{fe}|+C_{cmos}) \quad \text{(Eq. 2)}$$

With $|C_{fe}|$ negative and close and larger than $C_{cmos}$, the denominator of Eq. 3 becomes smaller and makes $V_2/V_1 \gg 1$.

To demonstrate voltage amplification is achieved in the ISFET with the negative charge layer:

$$C_{sense}(Vg-V_1)=C_{cmos}(V_2)$$

$$Vg-V_1=(C_{cmos}V_2)/C_{sense}$$

$$Vg/V_2-V_1/V_2=C_{cmos}/C_{sense}$$

$$Vg/V_2=C_{cmos}/C_{sense}+V_1/V_2 \quad \text{(Eq. 4)}.$$

To ensure that $V_2>Vg$, $C_{sense}$ has to be $\gg C_{cmos}$ and $V_1/V_2 \ll 1$ so that the sum of terms in Eq. 4 is <1. $V_1/V_2=|C_{fe}|/(C_{cmos}+|C_{fe}|)$ and voltage gain of 2-10 has been demonstrated. For a 50 Å sensing membrane of $Al_2O_3$ and a gate oxide of $SiO_2$ of 70 Å and $V_2/V_1=5$, it is shown from Eq. 4 that $Vg/V_2=0.48$, i.e., amplification of 2.1 can be achieved. Also, $0<C_{cmos}/|C_{fe}|<1$ and $C_{sense}/C_{cmos}>1$.

Figure 8:
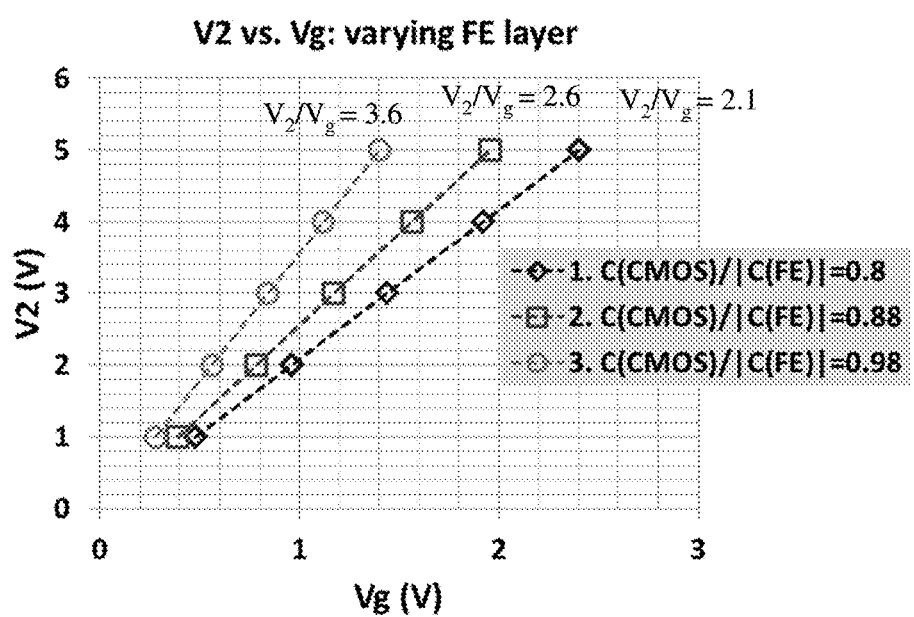
FIG. 8 shows a graph of $V_2$ vs. Vg with a varying layer of ferroelectric material.

FIG. 8 shows a graph of $V_2$ vs. Vg with a varying layer of ferroelectric material. In the graph of FIG. 8, the y-axis is $V_2$ in volts and the x-axis is Vg in volts. In the structure used for the graph of FIG. 8, the gate dielectric material is oxide material having a thickness of 70 Å and the sensing membrane is $Al_2O_3$ having a thickness of 50 Å. By varying the layer of the ferroelectric material, it is shown that the ratio of $C_{cmos}/|C_{fe}|$ increases: 0.8, 0.88 and 0.98.

Figure 9:
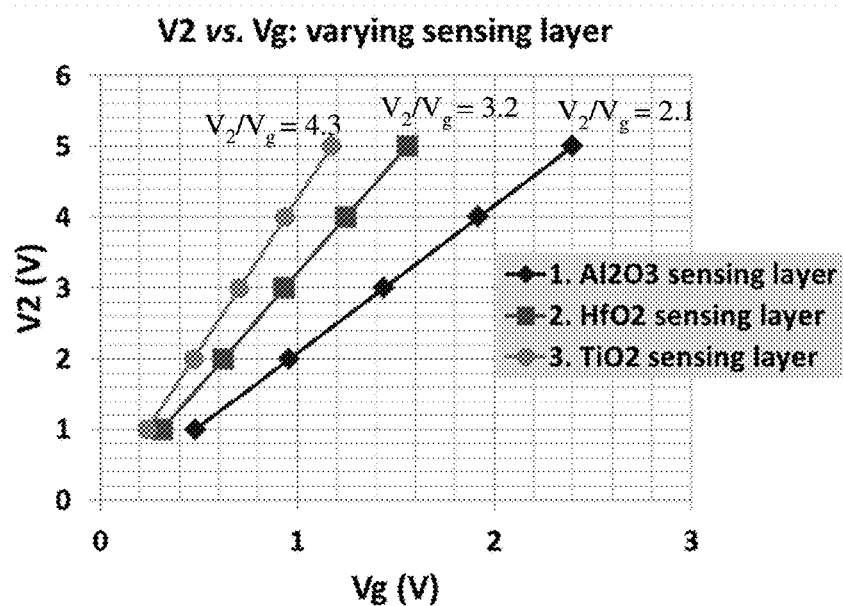
FIG. 9 shows a graph of $V_2$ vs. Vg with a varying sensing membrane.

FIG. 9 shows a graph of $V_2$ vs. Vg with a varying sensing membrane. In the graph of FIG. 9, the y-axis is $V_2$ in volts and the x-axis is Vg in volts. In the structure used for the graph of FIG. 9, the gate dielectric material is oxide material having a thickness of 70 Å and the sensing membrane is $Al_2O_3$, $HfO_3$ or $TiO_2$. As shown in this graph, the k-value of the different sensing members will increase. Even larger voltage amplification ($V_2/Vg$) can be achieved by: increasing $C_{cmos}/|C_{fe}|$ ratio ($|C_{fe}|>C_{cmos}$), and/or increasing $C_{sense}$ (using higher-k materials, e.g., $HfO_2$ ($\varepsilon r=25$) or $TiO_2$ ($\varepsilon r=80$)) over Ccmos.

The method(s) as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A structure comprising:
   a substrate comprising a doped region;
   a gate dielectric material directly on the doped region;
   a ferroelectric material directly on the gate dielectric material;
   a dielectric layer directly on the substrate and surrounding the gate dielectric material and the ferroelectric material;
   a trench in the dielectric layer; and
   a sensing membrane lining the trench of the dielectric layer and directly on the ferroelectric material within the trench.

2. The structure of claim 1, wherein the gate dielectric material, the ferroelectric material and the sensing membrane are connected in series.

3. The structure of claim 2, wherein the series connection of the gate dielectric material, the ferroelectric material and the sensing membrane form a negative capacitance ion sensitive field effect transistor (ISFET).

4. The structure of claim 1, wherein the gate dielectric material is $SiO_2$.

5. The structure of claim 1, wherein the ferroelectric material is one of lead zirconate titanate (PZT), $PbZr/TiO_3$, $BaTiO_3$, $PbTiO_3$, lead lanthanum zirconate titanate (PLZT), and $SrBi_2Ta_2O_9$.

6. The structure of claim 1, wherein the sensing membrane is one of $Al_2O_3$, $HfO_3$ and $TiO_2$.

7. The structure of claim 1, wherein the structure achieves an amplification of 2.1.

8. The structure of claim 1, wherein $C_{sense}$ is representative of a capacitance of the sensing membrane, $|C_{fe}|$ is representative of a capacitance of the ferroelectric material and $C_{cmos}$ is representative of the capacitance of the gate dielectric material and/or substrate, and $0<C_{cmos}/|C_{fe}|<1$ and $C_{sense}/C_{cmos}>1$.

9. The structure of claim 1, wherein the doped region is a p-well.

10. A structure comprising:
 a substrate comprising a doped region;
 a gate dielectric material over the doped region;
 a ferroelectric material over the gate dielectric material; and
 a sensing membrane over the ferroelectric material,
 wherein the substrate, gate dielectric material, the ferroelectric material and the sensing membrane are a nanowire.

11. A negative capacitance ion sensitive device comprising a gate dielectric material, a ferroelectric material and a sensing membrane electrically connected in series wherein:
 the gate dielectric material is over a doped region of a substrate;
 the ferroelectric material is over the gate dielectric material;
 the sensing membrane is over the ferroelectric material; and
 the substrate, gate dielectric material, the ferroelectric material and the sensing membrane are a nanowire.

12. The negative capacitance ion sensitive device of claim 11, wherein the gate dielectric material is $SiO_2$.

13. The negative capacitance ion sensitive device of claim 11, wherein the ferroelectric material is one of lead zirconate titanate (PZT), $PbZr/TiO_3$, $BaTiO_3$, $PbTiO_3$, lead lanthanum zirconate titanate (PLZT), and $SrBi_2Ta_2O_9$.

14. The negative capacitance ion sensitive device of claim 11, wherein the sensing membrane is one of $Al_2O_3$, $HfO_3$ and $TiO_2$.

15. The negative capacitance ion sensitive device of claim 11, wherein $C_{sense}$ is representative of a capacitance of the sensing membrane, $|C_{fe}|$ is representative of a capacitance of the ferroelectric material and $C_{cmos}$ is representative of the capacitance of the gate dielectric material and/or substrate, and $0<C_{cmos}/|C_{fe}|<1$ and $C_{sense}/C_{cmos}>1$.

16. The structure of claim 1, further comprising a passivation layer on the dielectric layer.

17. The structure of claim 16, wherein the trench is in the passivation layer.

18. The structure of claim 17, wherein the sensing membrane lines the passivation layer within the trench.

* * * * *